(12) United States Patent
Hirose et al.

(10) Patent No.: US 10,478,144 B2
(45) Date of Patent: Nov. 19, 2019

(54) X-RAY IMAGING APPARATUS AND IMAGING METHOD USING THE SAME

(71) Applicant: SHIMADZU CORPORATION, Nakagyo-ku, Kyoto-shi, Kyoto (JP)

(72) Inventors: Dai Hirose, Kyoto (JP); Koki Yoshida, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 246 days.

(21) Appl. No.: 15/796,927

(22) Filed: Oct. 30, 2017

(65) Prior Publication Data

US 2018/0177480 A1 Jun. 28, 2018

(30) Foreign Application Priority Data

Dec. 28, 2016 (JP) .................................. 2016-254996

(51) Int. Cl.
*A61B 6/00* (2006.01)
*A61B 6/04* (2006.01)

(52) U.S. Cl.
CPC ............ *A61B 6/547* (2013.01); *A61B 6/0407* (2013.01); *A61B 6/0457* (2013.01); *A61B 6/481* (2013.01); *A61B 6/487* (2013.01); *A61B 6/504* (2013.01)

(58) Field of Classification Search
None
See application file for complete search history.

(56) References Cited

FOREIGN PATENT DOCUMENTS

JP 2014-223175 12/2014

*Primary Examiner* — Edwin C Gunberg
(74) *Attorney, Agent, or Firm* — Andrew F. Young, Esq.; Lackenbach Siegel, LLP

(57) ABSTRACT

An X-ray imaging apparatus enables to improve workability and a register of a pathway information on X-ray imaging. The X-ray imaging apparatus comprises a control element that control a driving element 5 so that the X-ray irradiation element to image a subject S and a table loading the subject S are relatively movable based on a pathway information that is pre-registered when imaging the subject S. The control element acquires the information as a representative point relative to the location at which the table and the X-ray irradiation detection element 1 suspend to move relatively based on that relative moving between the table 2 and the X-ray irradiation element suspends; or that once the relative moving between the table 2 and the X-ray irradiation detection element suspends, the relative moving between the table and the X-ray irradiation detection element restarts, after the X-ray irradiation detection element and the table are relatively moved, and registers the pathway information based on the acquired representative point.

13 Claims, 11 Drawing Sheets

Non-pressing down state
(Table locked state)

Pressing down state
(Table unlocked state)

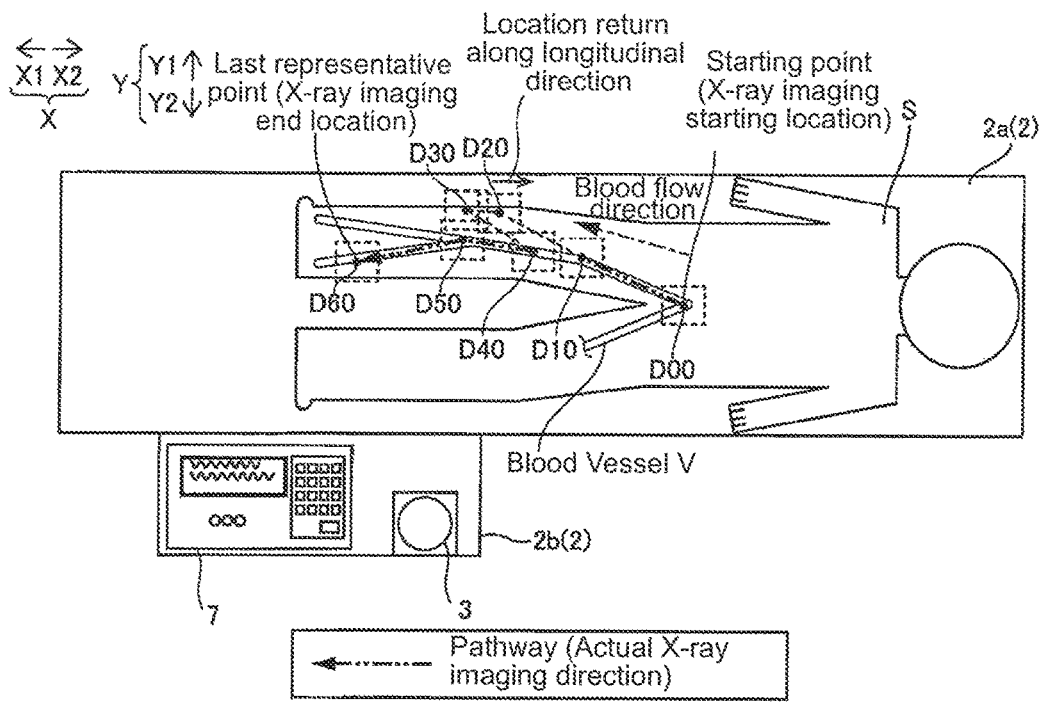
FIG. 6A  Acquisition of representative point
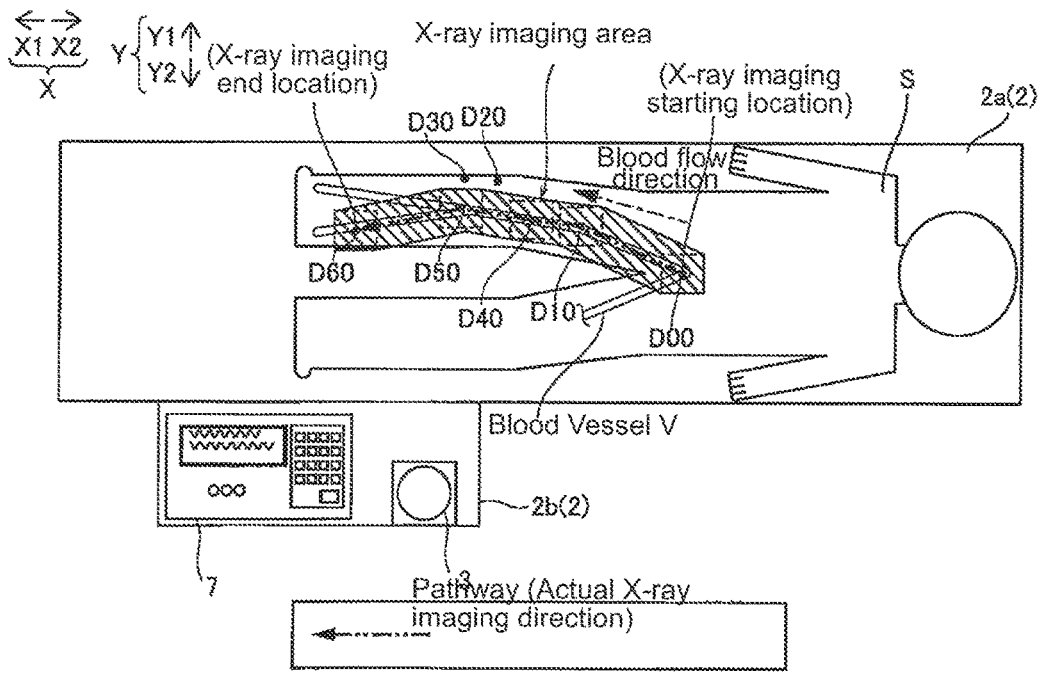
FIG. 6B  Actual X-ray imaging

FIG. 7A Acquisition of representative point
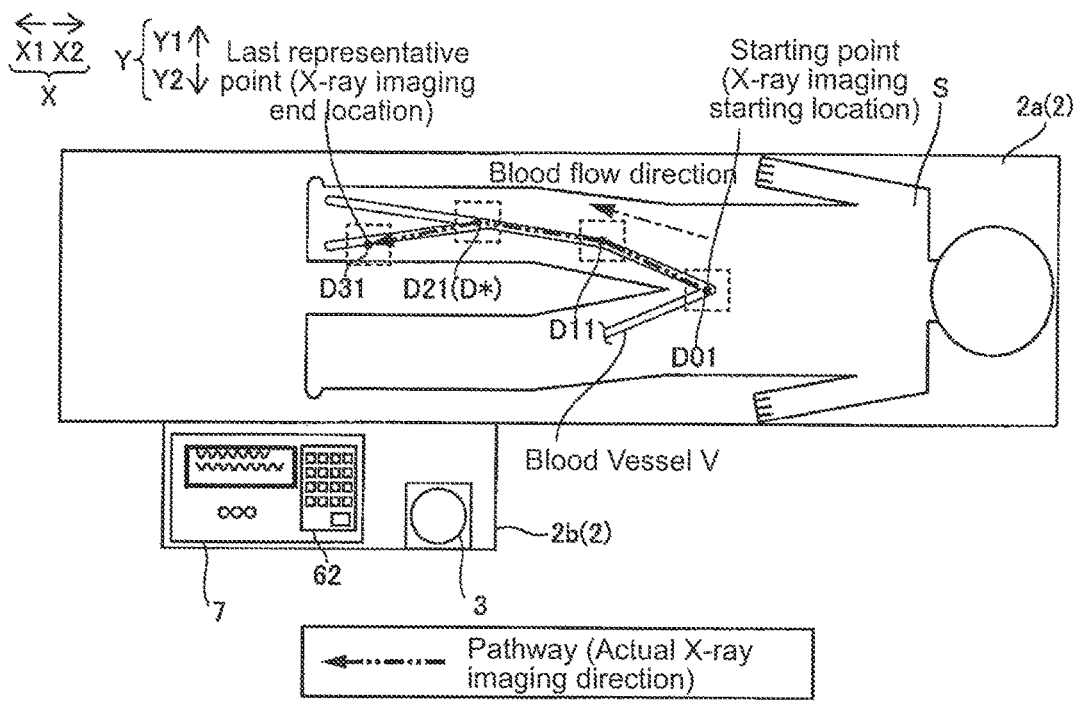
FIG. 7B Actual X-ray imaging
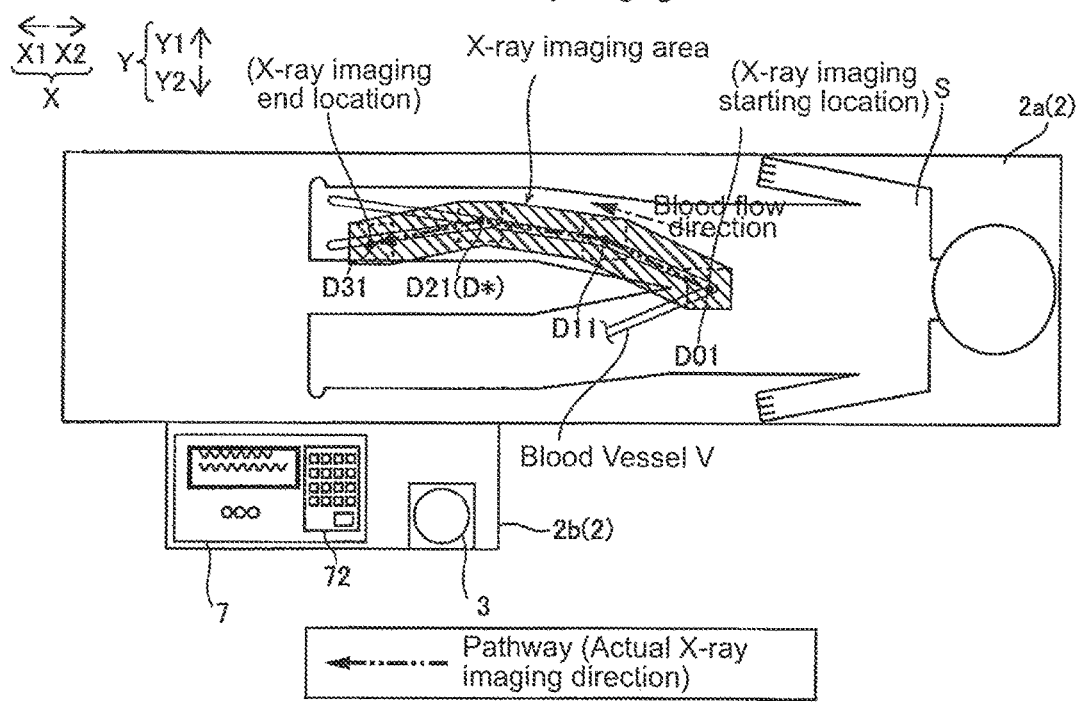

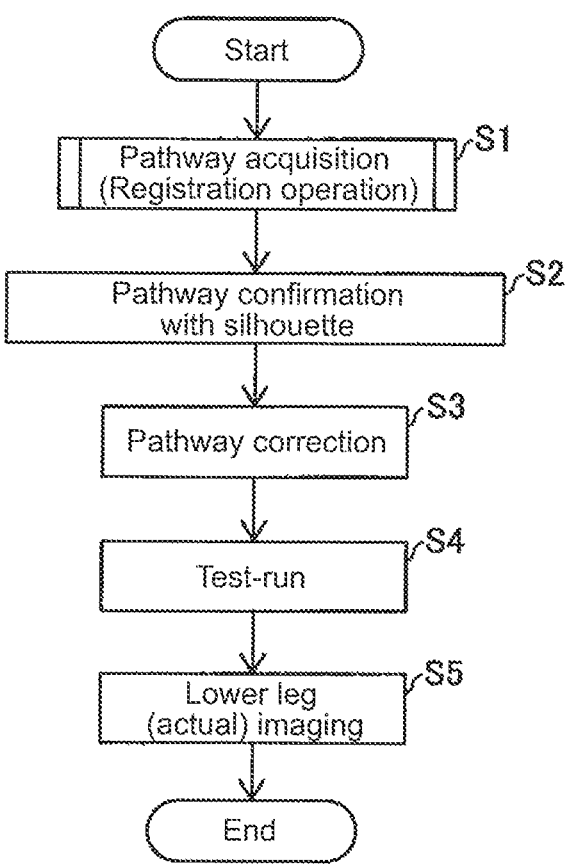
FIG. 8  X-ray Imaging Processing

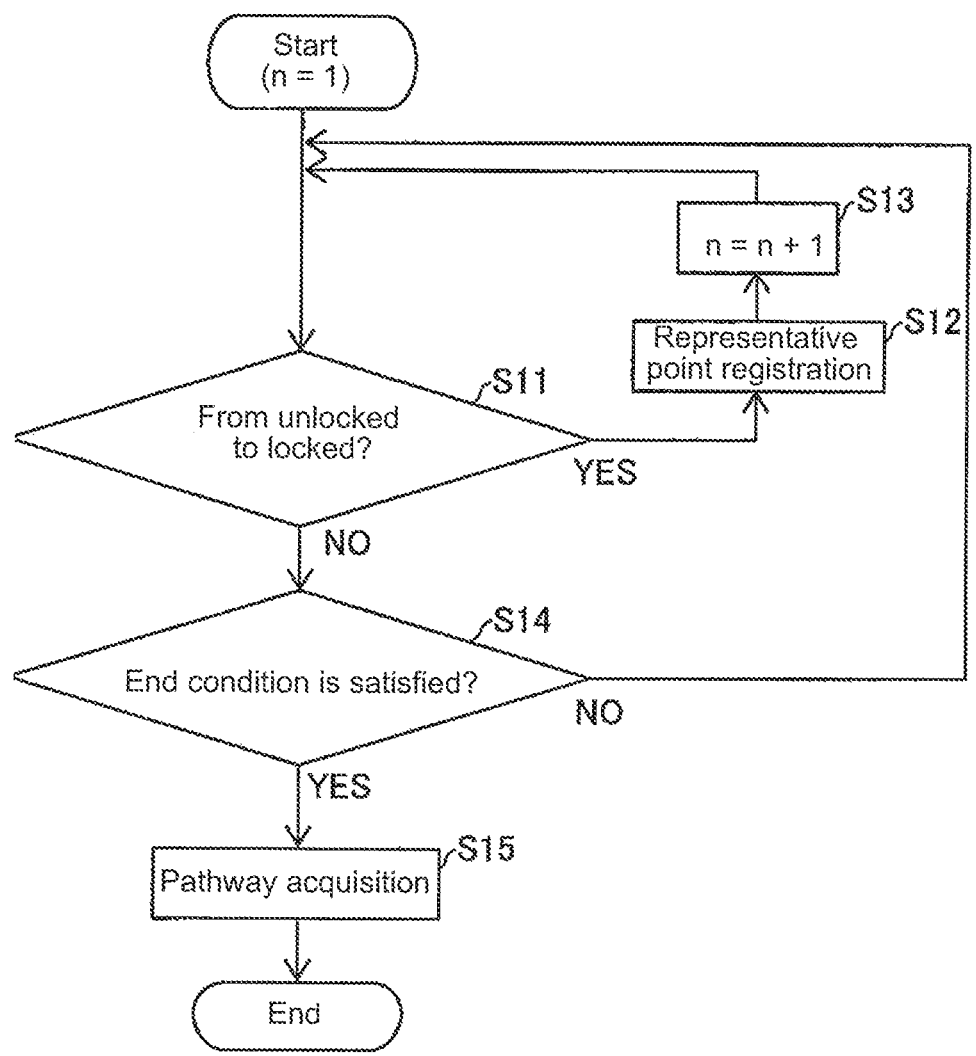

X-RAY IMAGING APPARATUS AND IMAGING METHOD USING THE SAME

CROSS REFERENCE TO RELATED APPLICATIONS

This application relates to and claims priority from JP 2016-254996 filed Dec. 28, 2016, the entire contents of which are incorporated herein by reference.

FIGURE SELECTED FOR PUBLICATION

FIG. 4

BACKGROUND OF THE INVENTION

Field of the Invention

The present invention relates to an X-ray imaging apparatus and an imaging method of the X-ray imaging apparatus, and particularly relates to the X-ray imaging apparatus and the imaging method using the X-ray imaging apparatus that is structured so that the table, on which a subject is loaded, is relatively-movable relative to an X-ray irradiation detection element.

Description of the Related Art

Conventionally, it is known that an X-ray imaging apparatus is structured so that the table, on which a subject is loaded, is relatively-movable relative to an X-ray irradiation detection element (e.g., Patent Document 1).

The above Patent Document 1 discloses the X-ray imaging apparatus that comprises the X-ray irradiation element, which irradiates an X-ray to a subject, the X-ray imaging element (X-ray detection element), which images the subject based on the X-ray transmitting the subject, and the imaging platform (table) that is relatively-movable relative to the X-ray irradiation element and the X-ray imaging element (X-ray detection element) while the subject is being loaded, and a memory, which stores the data relative to the imaging. According to such X-ray imaging apparatus, the control element stores the trace (trajectory) of an imaging platform (table) relatively moved to image the lower left leg in the memory, and also relatively moves the imaging platform (table) to image the lower right leg in accordance with the mirror trajectory from the starting point based on the moving information stored in the memory.

Here, as the input of the moving information; for example, it can be operative to register the location as a representative point, at which the imaging platform suspends, by suspending moving of the table and pressing down the registration switch after locking of the imaging platform (table) is unlocked by pressing down the unlocking-switch and the imaging platform is moved to the desired location. In addition, a plurality of representative points is registered by repeating such operation multiple times. Then, imaging the subject is implemented by relatively moving the imaging platform along the plurality of registered representative points relative to the X-ray irradiation element and the X-ray imaging element.

RELATED PRIOR ART DOCUMENTS

Patent Document

Patent Document 1: JP Patent Published 2014-223175

ASPECTS AND SUMMARY OF THE INVENTION

Objects to be Solved

However, according to the conventional method, in which a plurality of representative points is registered and the imaging platform relatively moves along a plurality of the registered representative points relative to the X-ray irradiation element and the X-ray imaging element, a user must implement both operations of pressing down the unlock-switch (moving of the imaging platform) and pressing down the registration switch every one of representative points. Therefore, relative to the registration of the moving information (pathway information), it is problematic that a user has to do more works (workability is poor.)

The present invention has been proposed in order to solve the aforementioned problems, and an object of the present invention is to provide an X-ray imaging apparatus that can improve workability relative to the work to register a pathway information and an imaging method using the X-ray imaging apparatus.

Means for Solving the Problem

For an achievement of the above purpose, an X-ray imaging apparatus according to the first aspect of the present invention comprises; an X-ray irradiation detection element including an X-ray irradiation element that irradiates an X-ray and an X-ray detection element that detects the X-ray transmitting the subject; a table that can load the subject on the loading plane; a driving element that relatively moves the table relative to an X-ray irradiation detection element; and a control element that controls to move at least one of the table and the X-ray irradiation detection element by the driving element based on the pre-registered pathway information; wherein the control element acquires the information, as a representative point, relative to the location at which the table and the X-ray irradiation detection element suspend, to move relatively based on that relative moving between the table and the X-ray irradiation element suspends; or that once the relative moving between the table and the X-ray irradiation detection element suspends, the relative moving between the table and the X-ray irradiation detection element restarts after the table and the X-ray irradiation detection element are relatively moved manually or by the driving element, and registers the pathway information based on the acquired representative point.

The X-ray imaging apparatus according to the first aspect of the present invention as set forth above, the control element acquires the information, as a representative point, relative to the location at which the table and the X-ray irradiation detection element suspend moving relatively based on that relative moving between the table and the X-ray irradiation element suspends; or that once the relative moving between the table and the X-ray irradiation detection element suspends, the relative moving between the table and the X-ray irradiation detection element restarts after the table and the X-ray irradiation detection element are relatively moved manually or by the driving element, and registers the pathway information based on the acquired representative point. Therefore, the representative point is automatically acquired (i.e., the pathway information is automatically registered) based on that relative moving between the table and the X-ray irradiation element suspends, or that once the relative moving between the table and the X-ray irradiation detection element suspends, the relative moving between the table and the X-ray irradiation detection element restarts, so that the user (imaging operator) does not have to press down such as a registration switch and so forth to register the representative point and workability in association with the work related to registration of the pathway information can be improved. Further, according to the present invention, "manually" is a broad aspect including not only the event in which the user (imaging operator and so forth) presses down the switch, but also the event in which the user presses the table or the X-ray irradiation detection element with a body or a foot.

The X-ray imaging apparatus according to the first aspect of the present invention, as set forth above, preferably comprises an unlocking element that allows the table and the X-ray irradiation detection element to relative move when unlocking the locked table and setting the table movable, wherein the control element acquires the information of the location, at which the table suspends, based on that; the unlocking element unlocks the locked table and the table moves, and the unlocking element changes locking of the table from the unlocked state to the locked state; or that the unlocking element changes locking of the table from the unlocked state to the locked state and again the table is unlocked, as the representative point; and also registers the pathway information based on the acquired representative point. According to such aspect, the representative point is automatically acquired (i.e., the pathway information is automatically registered) based on that, the unlocking element changes locking of the table from the unlocked state to the locked state; or that the unlocking element changes locking of the table from the unlocked state to the locked state and again the table is unlocked, so that the user can improve workability of a work to register the pathway information as much as that the user does not have to press down the registration switch and so forth.

In such case, preferably, the control element acquires the representative point simultaneously when the unlocking element changes locking of the table from the unlocked state to the locked state based in the case of that the representative point is acquired based on that the unlocking element changes locking of the table from the unlocked state to the locked state. In such aspect, the control element acquires the representative point only by that the imaging operator decides the relative location of the table and locks the table at the adequate location relative to the desired pathway, so that the operator can register easily the pathway information. Further, "simultaneously" means a broad definition including an "approximately simultaneously" on which a there is more or less a time lag.

According to the X-ray imaging apparatus that acquires the information of the location, at which the table suspends, as the representative point based on that the table is in the unlocked state or the table is in the locked state, preferably, when the representative point is acquired based on that the unlocking element changes locking of the table from the unlocked state to the locked, the control element acquires representative point when the locked state is maintained for a predetermined period after the unlocking element changes locking of the table from the unlocked state to the locked state. Given such constitution, the control element acquires representative point when the locked state is maintained for the predetermined period after the unlocking element changes locking of the table from the unlocked state to the locked state, so that it can be prevented that the representative point is immediately registered even when the user erroneously sets the unlocking element to the locked state.

According to the X-ray imaging apparatus that acquires the information of the location, at which the table suspends, as the representative point based on that the table is in the unlocked state or the table is in the locked state, it is preferable that the unlocking element comprises an unlocking switch that sets locking of the table under the unlocked state while being pressed down. According to such aspect, the table moves only while the unlocking switch is being pressed down, so that the table would not relatively move when the user does not press down the unlocking switch. Accordingly, an unintentional moving of the table against the user can be prevented.

According to the X-ray imaging apparatus of the first aspect set forth above, it is preferable that the control element registers the pathway information based on a plurality of representative points. According to such aspect, the imaging operator specifies a plurality of representative points along the imaging target region of the subject, so that the operator can easily set up the pathway, According to the X-ray imaging apparatus of the first aspect set forth above, it is preferable that the direction of relative moving of the table relative to the X-ray irradiation detection element comprises at least first and the second direction orthogonal to each other in the loading plane of the table among a plurality of directions crossing to one another. According to such aspect, when imaging the subject, the control element controls the driving element to move at least one of the table and the X-ray irradiation element based on the pathway information, which is pre-registered relative to both first direction and second direction orthogonal to each other, so that an occurrence of workload against the user, which is an operation to relatively move the table in the two directions including the first direction and the second direction, is preventable, when imaging.

According to the X-ray imaging apparatus of the first aspect set forth above, it is preferable that the X-ray imaging apparatus further comprises a plurality of direction specification elements that moves relatively the X-ray irradiation detection element and the table; wherein the direction specification element sets up the X-ray irradiation detection element and the table relatively movable and also specifies the direction in which the X-ray irradiation detection element and the table move relatively by the driving element; the control element moves at least one of the X-ray irradiation detection element at a predetermined rate in the direction specified by the direction specification element by the driving element while the direction, which the direction specification element specifies to relatively move the X-ray irradiation detection element by the direction specification element, becomes the specified operative condition, and in addition, the relative location, at which the X-ray irradiation detection element and the table suspend, is acquired as the representative point after the direction specification element is changed from the operative state to the non-operative state. According to such aspect, after the direction specification element is changed from the state in which the relative moving is specified to the state in which the relative moving is not specified, the control element acquires the relative location, at which the X-ray irradiation element and the table suspend, as the representative point, so that workability of the work to register the pathway information can be easily improved even when the X-ray irradiation element or the table is relatively moved by the driving element, not manually. In addition, the period "while the direction to relatively move the X-ray irradiation detection element and the table is being specified" includes, for example, not only the period in which the direction specification element corresponding to one direction is being specified, but also the period of a series of operations in which the direction specification element corresponding to the other direction is switched to be specified right after the direction specification element corresponding to the one direction is specified and the direction specification element corresponding to the other direction is specified and then is not being specified.

According to the X-ray imaging apparatus of the first aspect as set forth above, it is preferable that the control element stores the relative location of the X-ray irradiation detection element and the table, which is acquired in advance differently from the representative point, as a memory location; relatively moves the table and the X-ray irradiation detection element to the memory location by the driving element at the beginning of acquisition of a plurality of representative points or in the middle thereof; and also acquires the memory location as the representative point. According to such aspect, the representative point is acquired based on the memory location acquired in advance, so that a work to register can be eliminated. Particularly, when the memory location is a common point existing in an approximate same location relative to each subject (characteristic point common to a human body), the imaging operator can register the memory point regardless expertise thereof. Specifically, the pathway including the memory location can be easily obtained.

According to the X-ray imaging apparatus of the first aspect set forth above, it is preferable that when a plurality of representative points is acquired and when the second representative point is acquired so that the location of the representative point is returned along the longitudinal direction from the first direction and the second direction orthogonal to each other in the loading plane of the table following acquisition of one or the plurality of representative points, the control element does not use the first representative point, which is one or a plurality of representative points acquired prior to returning the location and is located in the traveled location farther from the second representative point in the longitudinal direction, to register the pathway information. According to such aspect, when the imaging operator acquires the deviated location from the desired pathway (i.e., erroneous location) as the first representative location, the operator can cancel the erroneously acquired first representative point without separately implementing a canceling operation for the erroneously acquired first representative point. Specifically, a work to register the pathway information can be eliminated.

According to the X-ray imaging apparatus of the first aspect set forth above, it is preferable that the X-ray imaging apparatus further comprises a velocity operation element that receives an operation to control the relative moving of the table and the X-ray irradiation detection element moving along the pathway based on the pathway information arid the control element controls the relative moving of the table and the X-ray irradiation detection element by the driving element based on the operation of the velocity operation element. According to such aspect, the user can implement the velocity control of the relatively moving of the table and the X-ray irradiation detection element by the driving element, so that the user facilitates to follow the imaging location on the pathway relative to the velocity of the moving imaging target when implementing an X-ray imaging of the moving imaging target, such as a contrast agent flowing in blood vessel of the subject.

According to the X-ray imaging apparatus of the first aspect as set forth above, it is preferable that the control element acquires the pathway based on the pathway information by interpolating the distance between representative points with a straight line or a curved line. According to such aspect, the imaging operator can set up easily the pathway by interpolating without specifying many representative points.

An imaging method using the X-ray imaging apparatus according to the second aspect of the present invention, in which the X-ray imaging apparatus comprises an X-ray irradiation detection element including an X-ray irradiation element that irradiates an X-ray to a subject and an X-ray detection element that detects the X-ray transmitting said subject and a table that can load the subject on the loading plane; of which the X-ray irradiation detection element and the table are relatively movable; comprises a step of acquiring the information, as a representative point, relative to the location at which the table and the X-ray irradiation detection element suspend to move relatively based on that relative moving between the table and the X-ray irradiation element is suspended; or that once the relative moving between the table and the X-ray irradiation detection element is suspended, the relative moving between the table and the X-ray irradiation detection element restarts after the table and the X-ray irradiation detection element are relatively moved; and a step of registering the pathway information based on the acquired representative point in advance, and a step of X-ray-imaging the subject while moving at least one of the table and the X-ray irradiation detection element by the driving element based on the pre-registered pathway information.

The imaging method of the X-ray imaging apparatus according to the second aspect of the present invention as set forth above, comprises; a step of acquiring the information, as a representative point, relative to the location at which the table and the X-ray irradiation detection element suspend to move relatively based on that relative moving between the table and the X-ray irradiation element is suspended; or that once the relative moving between the table and the X-ray irradiation detection element is suspended, the relative moving between the table and the X-ray irradiation detection element restarts after the table and the X-ray irradiation detection element are relatively moved; and a step of registering the pathway information in advance based on the acquired representative point. Therefore, the representative point is automatically acquired (the pathway information is automatically registered) based on that relative moving between the table and the X-ray irradiation element suspends, or that once the relative moving between the table and the X-ray irradiation detection element suspends and then the relative moving between the table and the X-ray irradiation detection element restarts, so that workability in association with the work related to registration of the pathway information can be improved as much as that the user does not have to press down the registration switch and so forth to register the representative point.

Effect of the Invention

According to the present invention, workability of a work to register the pathway information relative to an X-ray imaging can be improved.

The above and other aspects, features and advantages of the present invention will become apparent from the following description read in conjunction with the accompanying drawings, in which like reference numerals designate the same elements.

BRIEF DESCRIPTION OF THE DRAWINGS

FIGS. 6A, 6B are schematic views illustrating correction of the representative point acquired according to the aspect of the Embodiment 1 of the present invention.

FIGS. 7A, 7B are schematic views illustrating acquisition of the representative point acquired by a memory location according to the aspect of the Embodiment 1 of the present invention.

FIG. 8 is a flow-chart illustrating an X-ray imaging processing according to the aspect of the Embodiment 1 of the present invention.

FIG. 9 is a flow-chart illustrating a pathway acquisition processing according to the aspect of the Embodiment 1 of the present invention.

DETAILED DESCRIPTION OF THE PREFERRED EMBODIMENTS

Figure 1:
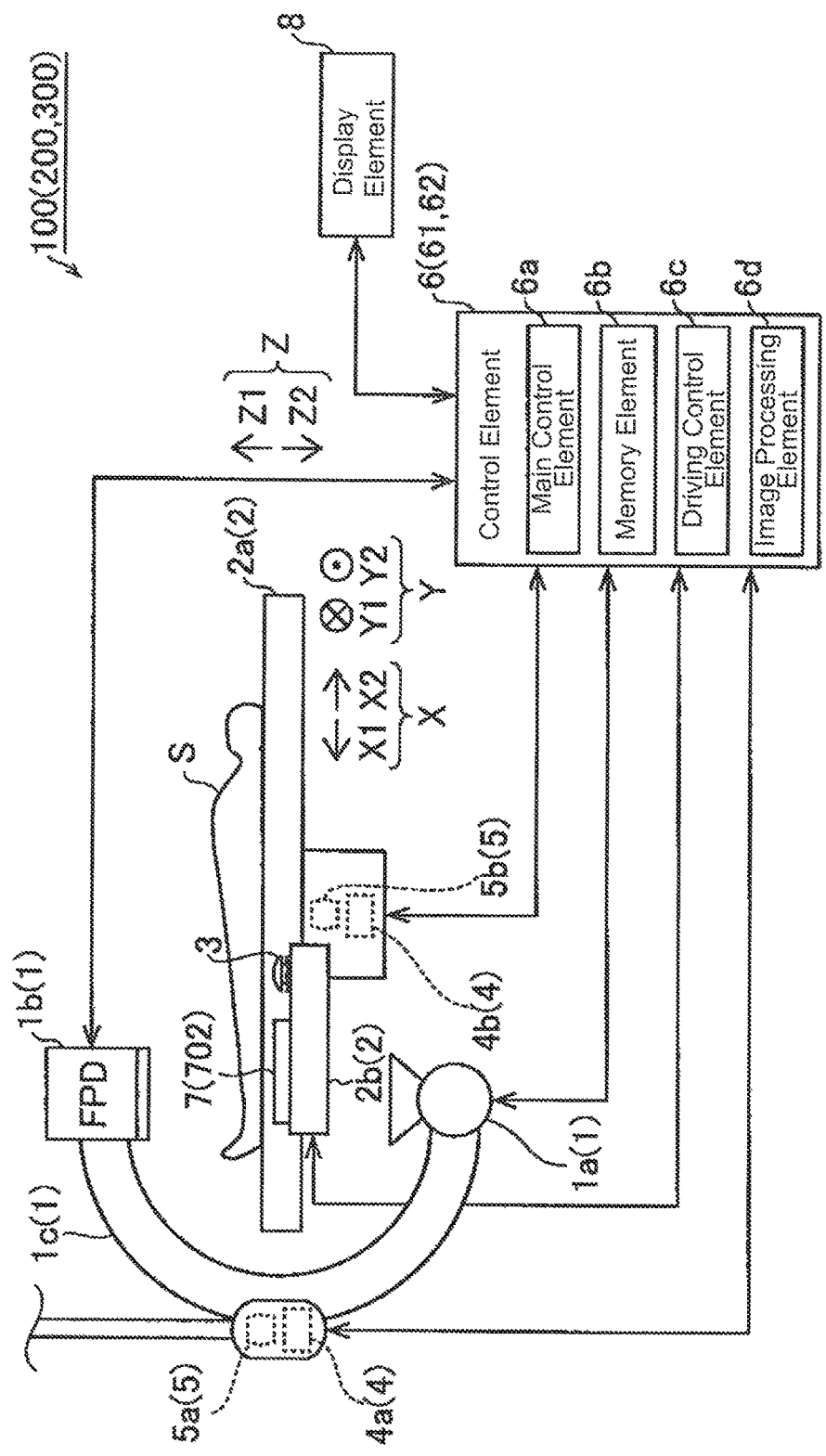
FIG. 1 is a schematic view illustrating an entire structure of an X-ray imaging apparatus according to the aspect of the Embodiment of the present invention.
Figure 2A:
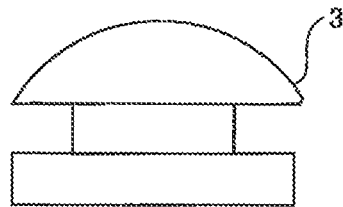
FIGS. 2A, 2B are schematic views illustrating a unlocking switch according to the aspect of the Embodiment 1 of the present invention.
Figure 2B:
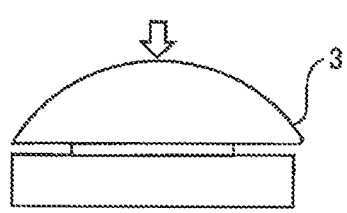
Figure 3:
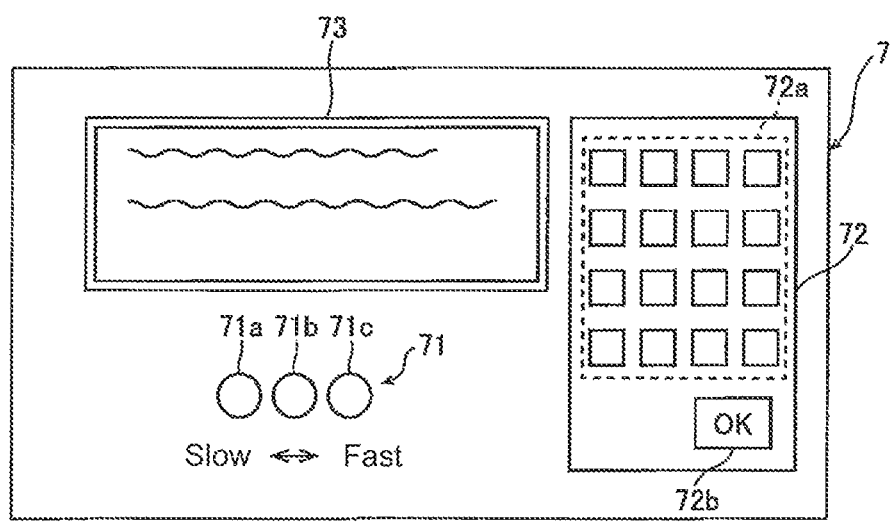
FIG. 3 is a schematic view illustrating an operation element according to the aspect of the Embodiment 1 of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, a "computer-based system" or computer operational system includes, without restriction or requirement some form of an input device for receiving data, an output device for outputting data in tangible form (e.g. printing or displaying on a computer screen or operational instructions), permanent memory for storing data as well as computer code, and a microprocessor for executing computer code wherein said computer code resident in said permanent memory will physically cause said microprocessor to read-in data via said input device, process said data within said microprocessor and output said processed data, via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention. Similarly, it will be understood that those of skill in this particular are particularly well versed in the use of programming and creation of programming (e.g., algorithms or operations including algorithms) and the use of data (e.g., information and information results etc.) that are enabled to work on the circuits and related chips, modules, features, and elements herein.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

Embodiment 1

Constitution of an X-Ray Imaging Apparatus)

First, referring to FIG. 1-FIG. 9, the inventor sets forth the constitution of the X-ray imaging apparatus 100 according to the aspect of the Embodiment 1 of the present invention.

An X-ray imaging apparatus 100 according to the aspect of the Embodiment 1 is structured to image (imaging or fluoroscopy) blood vessels of such as a lower leg and so forth of a subject S (a human subject to imaging) using a contrast agent. Further, the X-ray imaging apparatus 100 comprises an X-ray irradiation detection element 1, a table 2, a driving element 5, a control element 6, an operation element 7, and a display 8.

The X-ray irradiation detection element 1 comprises: an X-ray irradiation element 1a that irradiates an X-ray to a subject S, a detection element 1b that detects the X-ray transmitting through subject, and an arm 1c. The X-ray irradiation element 1a comprises e.g., an X-ray tube. The X-ray detection element 1b comprises e.g., FPD (flat panel detector). The arm 1c is driven by an irradiation detection element driving element 5a (set forth later) connected to an irradiation detection element driver 4a (set forth later).

The X-ray irradiation detection element 1 (X-ray irradiation element 1a and X-ray detection element 1b) starts imaging an X-ray image based on the directive for starting imaging input by an imaging operator (user) using the control element 6 through the operation element 7.

The X-ray irradiation element 1a irradiates an X-ray approximately vertically to the loading plane of the subject S. In addition, the X-ray detection element 1b detect the X-ray irradiated from the X-ray irradiation element 1a and transmitting the subject S, and acquires the X-ray image 1 based on the detected X-ray. Specifically, the X-ray detection element 1b converts the detected X-ray to an electric signal. In addition, the X-ray data converted to the electric signal is sent to the image processing element 6d.

The table 2 comprises a loading plane 2a and an operation base element 2b. In addition, the table 2 (loading plane 2a) is designed, on which the subject S can be loaded (as lateral decubitus) on the loading plane 2a (upper surface). In addition, the table 2 is relatively movable relative to the X-ray irradiation detection element 1 (X-ray irradiation element 1a and the X-ray detection element 1b).

The unlocking switch 3 is fixed to the operation base 2b and moves together with the table 2 (loading plane 2a). In addition, the unlocking switch 3 unlocks locking of the table 2 and includes a function to make the table 2 movable. Specifically, referring to FIG. 2A the unlocking switch 3 is unlocking locking of table 2 while being pressed down. In addition, referring to FIG. 2B, locking of table 2 is locked while not being pressed down (making the table 2 locked). Therefore, the imaging operator U unlocks locking of the table 2 by pressing down the unlocking switch 3 and, in addition, can move the table 2 in the horizontal direction (x-direction and y-direction) and the vertical direction (x-direction) while keeping the state, in which the unlocking switch 3 is being pressed down. In addition, when the imaging operator U suspends pressing down the unlocking switch 3 (the imaging operator U releases the hand from the unlocking switch 3), the unlocking switch 3 returns spontaneously to the un-pressed state due to such as a spring force. In addition, the unlocking switch 3 is an example of an "unlocking element" in the Claims.

The driver 4 comprises an irradiation detection element driver 4a that drives the irradiation detection element driving element 5a (set forth later) by supplying electric power and moves the X-ray irradiation detection element 1 thereby, and the table driver 4b that drives the table driving element 5b (set forth later) by supplying electric power and moves the table 2 thereby. In addition, when implementing an X-ray imaging (on an actual imaging), the irradiation detection driver 4a and the table driver 4b are operable to move respectively the X-ray irradiation detection element 1 and the table 2 along the desired pathway (i.e., relatively move the table 2 relative to the X-ray irradiation detection element 1) based on the registered pathway information set forth later. In addition, the moving velocities of the X-ray irradiation detection element 1 and the table 2 by the irradiation detection driver 4a and the table driver 4b are changeable by the velocity operation element 71 (set forth later) included in the operation element 7.

The driving element 5 comprises the irradiation detection element driving element 5a that drives the X-ray irradiation detection element 5a and the table driving element 5b that drives the table 2. The irradiation detection element driving element 5a moves (drives) the arm element 1c rotationally or translationally to image the loaded subject S from a variety of different angles. In addition, the table driving element 5b moves (drives) the table 2 in the x-direction and the y-direction orthogonal to each other in the loading plane and the perpendicular z-direction. In addition, the irradiation detection element 5a and the table driving element 5b comprises e.g., a motor. In addition, the x-direction and the y-direction are respectively a "first direction" and a "second direction' in the claims. Further, the x-direction is an example of "longitudinal direction" in the Claims.

The control element 6 further comprises a main control element 6a including such as a CPU (central processing unit) and so forth; a memory element 6b having a HDD (hard-disk drive), a memory and so forth; a driving control element 6c; and an image processing element 6d.

In addition, the control element 6 controls each element of the X-ray imaging apparatus 100. Specifically, the control element 6 controls the location and moving velocity driven by the irradiation detection element driving element 5a through the irradiation detection element driver 4a relative to the irradiation detection element 1, an X-ray irradiation intensity, an area (range), a direction and so forth. In addition, the control element 6 controls the location and moving velocity driven by the irradiation detection element driving element 5a through the table driver 4b relative to the table 2. In addition, the control element 6 controls the display element 8 to display a real-time image Ir when the subject S is fluoroscoped upon the registration operation of the pathway. In addition, the control element 6 controls the display element 8 to display an X-ray image I generated by the image processing element 6d. In addition, the control element 6 receives the operation through the operation element 7. In addition, the control element 6 directs the memory 6b to store the X-ray image.

Here, according to the aspect of the Embodiment 1, the control element 6 acquires the information, as a representative point, relative to the location at which the table 2 and the X-ray irradiation detection element 1 suspend to move relatively based on that relative moving between the table 2 and the X-ray irradiation element 1 suspends; or that once the relative moving between the table 2 and the X-ray irradiation detection element 1 suspends, the relative moving between the table 2 and the X-ray irradiation detection element 1 restarts after the X-ray irradiation detection element 1 and the table 2 are relatively moved manually or by the driving element 5, and registers the pathway information based on the acquired representative point.

Specifically, according to the aspect of the Embodiment 1, the control element 6 controls acquires the location information, at which the table 2 suspends, as a representative point and registers the pathway information based on the acquired representative point, based on that locking of the table 2 is unlocked by the unlocking switch 3 and table 2 moves and locking of the table 2 changes from the unlocked state to the locked state by the unlocking switch 3, or locking of the table 2 changes from the unlocked state to the locked state by the unlocking switch 3 and then again locking of the table 2 changes to the unlocked state. In addition, the inventor sets forth the detail of acquisition of the representative point (memory location set forth later) by the control element 6.

The memory element 6b stores a variety of programs executed by the main control element 6a, the driving control element 6c and the image processing element 6d; the data of the X-ray images I taken by the X-ray detection element 1b; the acquired representative point (set forth later); the memory location (set forth later); and the data relative to the registered pathway information (set forth later) and so forth.

The driving control element 6c controls the driving element 5 to control the location and the moving velocity of the X-ray irradiation detection element 1 (imaging location), and the location and the moving velocity of the table 2 (imaging location) through the driver 4. In addition, the driving control element 6c controls an X-ray irradiation of the X-ray irradiation element 1a. In addition, the driving control element 6c outputs the location information of the X-ray irradiation detection element 1 and the table 2 (information of imaging location) to the memory element 6b to be stored.

The image processing element 6d converts a plurality of X-ray images 1 taken with time to one long-image date or video data by connecting one another. In addition, the image processing element 6d executes an image processing including a contrast processing and a noise reduction processing on the X-ray image I to improve visual recognition and then outputs such improved images to the memory element 6b.

The operation element 7 comprises a velocity operation element 71. The velocity operation element 71 further comprises velocity operation switches 71a, 71b and 71c. The imaging operator U presses down velocity operation switches 71a, 71b and 71c and adjusts the velocity corresponding to each of relative velocity between the X-ray irradiation detection element 1 and the table 2. For example, the velocity operation switches 71a, 71b, 71c correspond to the slower (left) side, the slower relative moving velocity of the table 2, and the faster (right) side, the faster relative moving between the X-ray irradiation detection element 1 and the table 2. In addition, the velocity operation switches are not limited to 3. In addition, the velocity operation switch may include a suspension switch.

The operation element 7 comprises a keyboard element 72. The keyboard element 72 having a variety of keys 72a and a decision key 72b receives a variety of operation inputs from the imaging operator U. Specifically, the keyboard element 72 receives e.g., selection of the pathway and the memory location and so forth, in which the X-ray irradiation detection element 1 and table 2 move relatively on X-ray imaging, a directive to display the information of the subject (patient) S, the name given to the X-ray image I and so forth. In addition, the decision key 72b is the key to be pressed down when a variety of operations are determined. In addition, the operation element 7 includes a message window 73 that displays a variety of information.

The display element 8 displays a real-time image Ir acquired when the subject S is fluoroscoped upon the registration operation of the pathway. In addition, the display element 8 displays a pathway acquired based on the registration operation by the imaging operator U. Further, the display element 8 displays an X-ray image I that is imaged (I.e., taking an image) upon the actual X-ray imaging.

(X-Ray Imaging)

Next, the inventor sets forth an imaging of blood vessel V of the subject S using a contrast agent. Hereinafter, for convenience of simple explanation, the inventor sets forth the case in which only the table 2 moves and the table 2 relatively moves relative to the X-ray irradiation detection element 1 when acquiring the representative point and imaging.

The X-ray imaging apparatus 100 images the blood vessel V of the lower leg of the subject S who is supine on the table 2. Specifically, when imaging blood vessel V, the contrast agent is administered in the blood vessel of the lower leg of the subject S using a catheter (not shown in FIG.) and an X-ray image I is taken based, on the X-ray transmitting the subject S and detected by the X-ray detection element 1b. Accordingly, the blood vessel flow (blood vessel form) can be clearly imaged with the contrast agent through which an X-ray hardly pass.

In addition, the X-ray imaging apparatus 100 moves relatively the table 2 relative to the X-ray irradiation detection element 1 along the pre-registered pathway by the imaging operator U when the actual X-ray imaging is performed (i.e., imaging the contrast agent of blood).

(Registration of the Pathway Information)

Figure 4A:
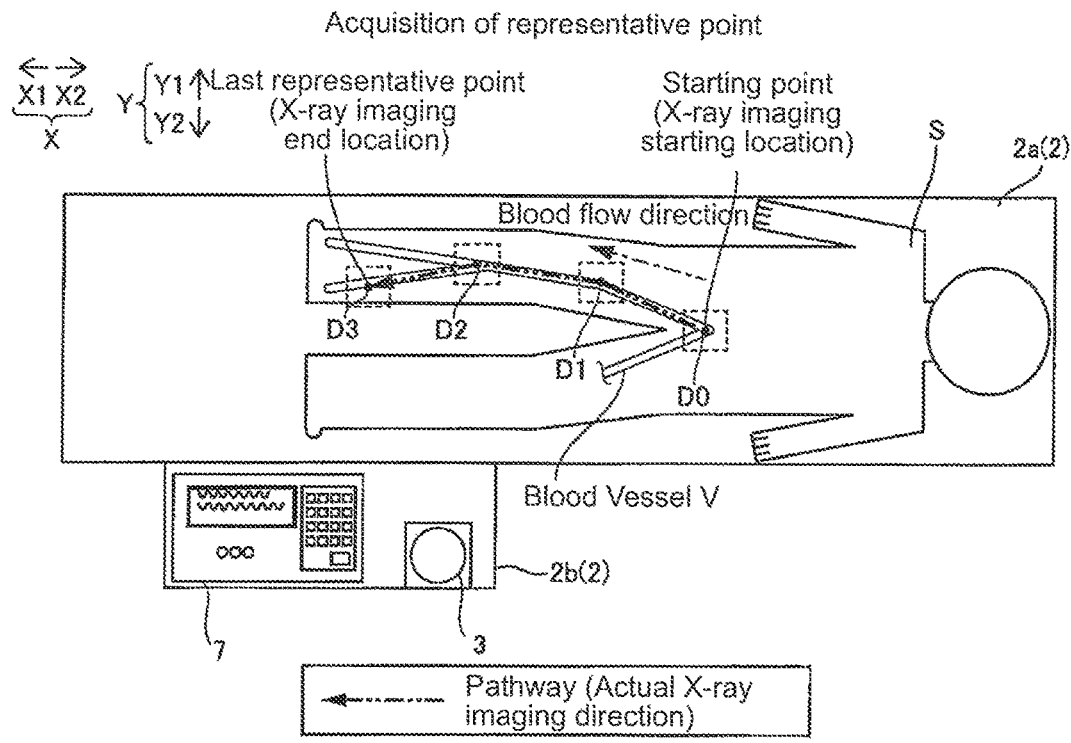
FIGS. 4A, 4B are schematic views illustrating registration of the representative point for the pathway information registration according to the aspect of the Embodiment 1 of the present invention.
Figure 4B:
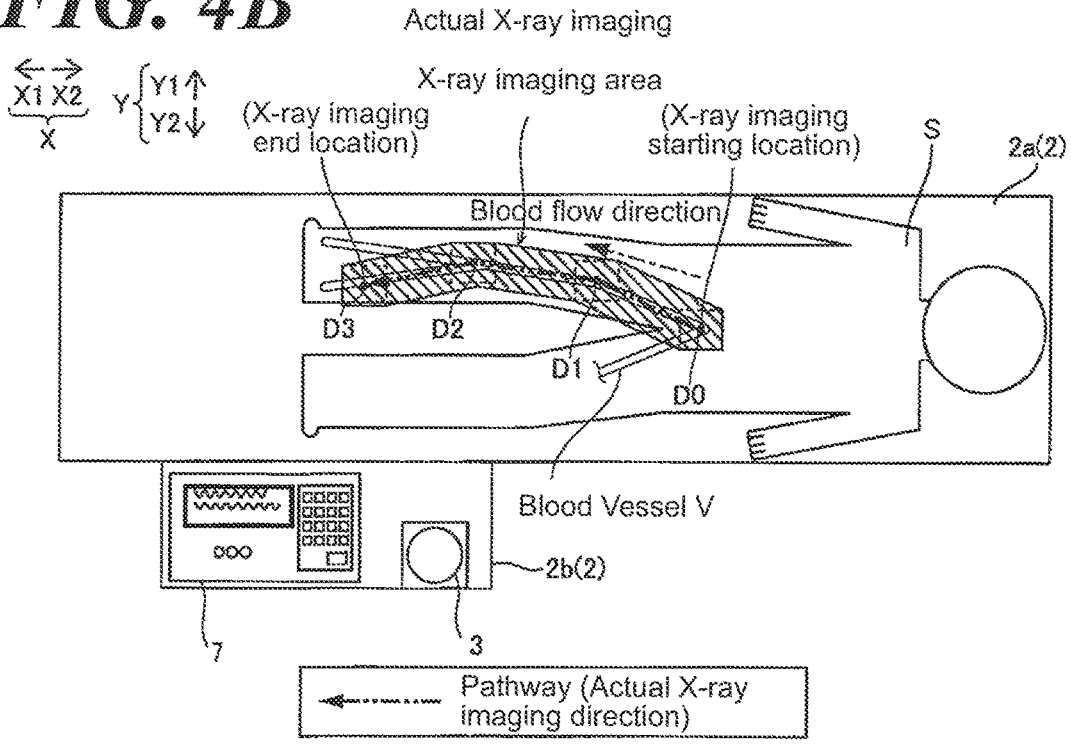
Figure 5:
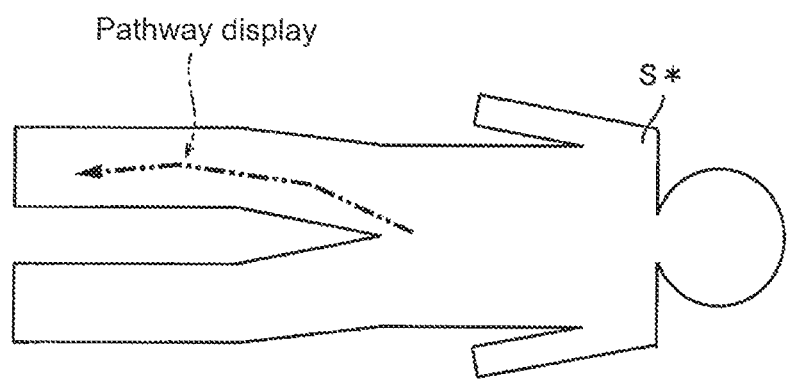
FIG. 5 is a schematic view illustrating confirmation of the pathway by superimposing a silhouette and the pathway information acquired according to the aspect of the Embodiment 1 of the present invention.

Referring to FIGS. 4, 5, the inventor sets forth an acquisition of the pathway information (representative point). As an example, referring to FIGS. 4A, 4B, the inventor sets forth the case in which the pathway information is registered from the starting point (first representative point) D0 and three representative points D1, D2, D3 and then X-ray imaging is implemented. The imaging operator U activates the mode to register the pathway information to the X-ray imaging apparatus 100 by an input operation relative to the operation element 7. At this time, a very weak X-ray is irradiated from the X-ray irradiation element 1a and the real-time image it is displayed on the display element 8 according to the data of X-ray transmitting the subject S and detected by the X-ray detection element 1b. The imaging operator U presses down the unlocking switch 3 (make the table 2 unlocked) while watching the real-time image Ir to move relatively the table 2 by the imaging operator per se (manually). And the imaging operator U moves the relative location of the table 2 as fitting the location (point), at which the imaging starts and the starting point of the pathway, in the center of the imaging range, suspends pressing down the unlocking switch 3 to make the table 2 locked. Therefore, the table 2 suspends and the information relative to the suspended location regarding the x-direction and the y-direction is stored in the memory element 6b as the starting point D0. Then, according to the aspect of the Embodiment 1, when the control element 6 acquires a representative point based on that locking of the table 2 is changed from the unlocked state to the locked state by the unlocking switch 3, the starting point D0 (as well as the representative points D1, D2) is simultaneously acquired when locking of the table 2 is changed from the unlocked state to the locked state by the unlocking switch 3.

Next, the imaging operator U selects a few adequate locations (points) on the virtual pathway and presses down the unlocking switch 3 (make the table 2 unlocked) while watching the real-time image Ir to move again relatively the table 2 by the imaging operator U per se (manually). And the imaging operator U moves the relative location of the table 2 as fitting the adequate location (point), which is on the virtual pathway, in the center of the imaging area, suspends pressing down the unlocking switch 3 to make the table 2 locked. Accordingly, the table 2 suspends and the information relative to the suspended location regarding the x-direction and the y-direction is stored in the memory element 6b as the representative point D1.

Further, while being pressed down (making the table 2 unlocked), the table 2 relatively moves to the imaging end location, and the location at which the table 2 suspends by ceasing pressing down the unlocking switch 3 (i.e., the location at which the table 2 suspends under the locked state) is stored in the memory element 6b. as the representative point D2. The representative point D3 that is the imaging end point is stored in the memory element 6b by repeating the same operation.

According to the aspect of the Embodiment 1 as set forth above, the control element 6 registers a pathway information based on a plurality of representative points D1-D3. Specifically, the control element acquires the pathway based on the pathway information by interpolating the distance between D1-D3 with a straight line or a curved line. For example, the control element 6 acquires the pathway on imaging based on the pathway information by interpolating the registered staring point D0, the representative points D1, D2 with the straight line. In addition, the control element 6 relatively moves the X-ray irradiation detection element 1 and the table 2 along the representative points in order in which the representative points are specified. Specifically, the control element 6 implements an X-ray imaging in series (D1, D2, D3 in order) firstly specified representative point from the starting point D0 upon the actual X-ray imaging. Accordingly, the pathway indicated by the thick 2-dots-dashed-line in FIGS. 4A, 4B is acquired. In addition, at lease starting point and one representative point are acquired to acquire the pathway.

The control, element 6 implements a test-run to make sure that the relatively moving X-ray irradiation detection element 1 and the table 2 are not going to interfere each other when the registration operation is implemented. In addition, the control element 6 starts the test-run from the ending location of the registration operation and ends the test-run at the starting location of the registration operation. Specifically, the control element 6 implements the test-run in the reverse tracking of the tracking of relative moving of the table 2 relative to the X-ray irradiation detection element 1 upon implementing the registration operation. For example, when the registration operation starts from the right groin (staring point D0) and ends at the right toe (representative point D3), the control element 6 starts the test-nm from the right toe and ends the test-run at the right groin. As results, when the test-run ends, the location of the X-ray irradiation detection element 1 relative to the table 2 returns to the starting location of the X-ray imaging, so that the location of the X-ray irradiation detection element 1 relative to the table 2 is not required to be moved from the end location of the registration operation only just for starting the X-ray imaging. Accordingly, the time needed for an X-ray imaging can be shorted.

Referring to FIG. 5, the control element 6 superimposes the schematic silhouette S* of the subject S (refer to FIG. 1) and the acquired pathway and as-is displays on the display element 8 (refer to FIG. 1) to make sure the general location of the pathway when the registration operation is implemented. In addition, the control element 6 superimposes the schematic silhouette S* of the subject S and the acquired pathway and in addition, superimposes a long image (e.g., an image of blood vessel) obtained by the fluoroscopy thereon and displays on the display element 8 when the fluoroscopy is performed (X-ray irradiation) upon implementing the registration operation. In addition, the pathway information is displayed in series until the acquired representative point even in the middle of acquiring the representative point.

(Correction of the Representative Point)

Next, referring to FIG. 6, the inventor sets forth a correction when a wrong representative point is registered when acquiring the, representative point.

Here, according to the aspect of the Embodiment 1, when the second representative point is acquired so that the location of the representative point is returned along the x-direction as the longitudinal direction among the x-direction and the y-direction orthogonal to each other in the loading plane of the table 2 following acquisition of one or a plurality of representative points when a plurality of representative points are acquired, the control element does not use the first representative point, which is the first representative point acquired prior to returning the location and is located in the traveled location farther from the second representative point in the x-direction, to register the pathway information.

Specifically, referring to FIG. 6A, the imaging operator U acquires the starting point D00, the representative point D10, the representative point D20, and the representative point D30. At this time, given the representative point D20, D30 are the location shifted from the expected pathway, the imaging operator U decides that such representative points must be corrected. In such case, the imaging operator U moves the table 2 in the returning direction (x2-direction) relative to the longitudinal direction of imaging, i.e., x-direction, while pressing down the unlocking switch 3 (i.e., making the table 2 unlocked) and suspends pressing down the unlocking switch 3 (i.e., making the table 2 locked) after the table 2 is moved to the relative location so that the approximate center of the imaging area is on the expected pathway. Consequently, the information relative to the location at which the table 2 suspends is acquired as the representative point D40. And the imaging operator U subsequently acquires the representative points D50, D60 and ends the processing to acquire the representative point. Thereby, referring to FIG. 6B, the imaging is implemented using the pathway acquired based on the representative point excluding the representative points D20, D30. Further, the representative points D20, D30 are one example of the first representative point in the claims. In addition, the representative point D40 is one example of the second representative point in the claims. In addition, the representative point of which location is returned in the longitudinal direction may not be omitted by the imaging operator U.

(Acquisition of a Representative Point Due to a Memory Location)

Next, referring to FIG. 7, the inventor sets forth an acquisition of the memory location D*. The control element 6 stores the relative location of the table 2, which is acquired in advance separately from the representative points, as the memory location D*, moves the table 2 to the memory location by the table driving element 5b at the beginning of acquisition of a plurality of representative points or in the middle thereof, and in addition, acquires the memory location D* as a representative point. The memory location D* is the information of the locations of X.-ray irradiation detection element 1 and the table 2, which is acquired in advance. The memory location D* may be, for example, a location stored regardless of a human body (subject S) and a common location that is approximately the same location relative to each subject is a interpolated bifurcation point or curve point of blood vessel V (blood pathway) based on the data related to a human body (empirical rule or statistics). In addition, the location information includes the data to identify the blood vessel V (pathway including the blood vessel which is a travel of general blood vessels and interpolated by a curve). In addition, the data that are identifying the information of the memory location D* and the blood vessel V (blood vessel pathway) are stored in the memory element 6b.

Referring to FIG. 7A, when acquiring the representative point, the imaging operator U retrieves the information of the memory location D* stored in the memory element 6b by executing an input operation relative to the operation element 7 (a keyboard 72 or a mouse not shown in FIG.) to move the table 2 to the location corresponding to the memory location D*. Then, the control element 6 acquires the memory location D* of the table 2, which is relatively moved, as a representative point. For example, referring to FIG. 7A, the second representative point D21 is acquired by that the memory location. D* is retrieved by the imaging operator U. In addition, the information from the starting point D01 to the first representative point D11 and the representative point D31 are acquired as the location information at which the table 2 suspends by that the imaging operator U moves relatively the table 2 manually. Consequently, the pathway of the actual imaging is as illustrated in FIG. 7B.

(X-Ray Imaging Processing)

Next, referring to FIG. 8, the inventor sets forth an X-ray imaging processing by the X-ray imaging apparatus 100 according to the aspect of the Embodiment 1.

At the step S1, the pathway information that moves relatively the table 2 relative to the X-ray irradiation detection element 1 by the registration operation. The inventor sets forth later the detail of the step S1.

At the step S2, the pathway is confirmed by using a silhouette S. Specifically, an image in which the schematic silhouette S* of the subject S (refer to FIG. 5) and the acquired pathway are superimposed is displayed on the display element 8 to make sure the position of the pathway. Further, the display element 8 displays the information relative to the representative point acquired from the starting point (a midway information of the pathway) every time when the representative point is acquired.

At the step S3, the pathway is corrected. Specifically, the acquired pathway is displayed on the display element 8. In addition, as a different correction method from the correction when the acquisition location of the representative point is returned to the longitudinal direction (x-direction), the pathway is corrected so that the pathway passes through the representative point after moving (correction) when the location of the representative point acquired by such as an operation of the mouse by the imaging operator U is moved (corrected).

At the step S4, a test-run is implemented. Specifically, when the registration operation starts from the groin of the right lower leg and ends at the right toe of the lower leg, the test-run starts from the right toe and ends at the right groin.

At the step S5, the X-ray imaging of the lower leg is performed by allowing the table 2 to move relatively relative to the X-ray irradiation detection element 1 along the acquired pathway. At this time, the imaging operator U adjusts the velocity of relative moving of the table 2 by the velocity operation element 71 in association with movement of a blood vessel contrast agent. And at the end location of imaging, the X-ray irradiation from the X-ray irradiation element 1a suspends and then the X-ray imaging processing ends.

(Pathway Acquisition Processing)

Referring to FIG. 9, the inventor sets forth a pathway acquisition processing (the sub-routine of the step S1) based on the registration operation by the X-ray imaging apparatus 100 according to the aspect of the Embodiment 1.

At the step S11, it is determined whether the first (number n) representative point is registered or not. Specifically, it is determined whether the representative point is registered due to switching from the state in which the unlocking switch 3 is being pressed down to the state in which not being pressed down or the representative point is registered due to retrieving the memory location D*, under the condition in which the table 2 is in-place at the location of the first (number n) representative point relative to the X-ray irradiation detection element 1. When the state of the unlocking switch 3 is changed from being pressed down to not being pressed down, or the memory location D* is retrieved, the step S12 is implemented to register the n-representative point. Then at the step S13, 1 is added to n and the step returns to the step S11. In addition, when the state of the unlocking switch 3 is not changed from being pressed down to not being pressed down or the memory location D* is not retrieved, the step 14 is implemented.

At the step S14, it is determined whether the condition to end the registration of the operation element 7 is satisfactory or not. Specifically, when the registration switch (e.g., a decision key 72b) is pressed down, the condition to end the registration is satisfactory and the step 15 is implemented. When the condition to end the registration is not satisfactory, the operation returns to the step 11. Further, when the number of acquisitions of the representative point (excluding the representative point of which location is returned in the longitudinal direction) meets the specified number pre-registered, the registration may end. In addition, while returning from the step S14 to the step S11, the starting point currently being acquired and the midway pathway to the representative point may be acquired.

At the step S15, the distance between a plurality of representative points excluding the representative point of which location is returned in the longitudinal direction is interpolated by the straight line, so that the pathway is acquired and then the pathway acquisition processing ends.

(Effect According to the Aspect of the Embodiment 1)

The following effect can be obtained according to the aspect of the Embodiment 1.

According to the aspect of the Embodiment 1, as set forth above, the control element 6 acquires the information of the location, as a representative point, at which the table 2 and the X-ray irradiation detection element 1 suspend to move relatively based on that relative moving between the table 2 and the X-ray irradiation element 1 suspends after the X-ray irradiation detection element 1 and the table 2 are relatively moved manually or by the driving element 5, and in addition, registers the pathway information based on the acquired representative point. Therefore, the representative point is automatically acquired (the pathway information is automatically registered) based on that relative moving between the table and the X-ray irradiation element suspends, or that once the relative moving between the table 2 and the X-ray irradiation, detection element 1 suspends, the relative moving between the table 2 and, the X-ray irradiation detection element 1 restarts, so that workability in association with the work related to registration of the pathway information can be improved as much as that the imaging operator U does not have to press down the registration switch and so forth to register the representative point.

In addition, according to the aspect of the Embodiment 1 as set forth above, the control element 6 acquires the location information, at which the table 2 suspends, as a representative point and registers the pathway information based on the acquired representative point based on that locking of the table 2 is unlocked by the unlocking switch 3 and table 2 moves and locking of the table 2 changes from the unlocked state to the locked state by the unlocking switch 3. According to such aspect, the representative point is automatically acquired (i.e., the pathway information is automatically registered) based on that the unlocking element changes locking of table 2 from the unlocked state to the locked state, so that the imaging operator U can improve workability of the work to register the pathway information as much as that the user does not have to press down the registration switch and so forth.

In addition, according to the aspect of the Embodiment 1 as set forth above, when acquiring a representative point based on that locking of the table 2 is changed from the unlocked state to the locked state by the unlocking switch 3, the control element 6 simultaneously acquires a representative point when locking of the table 2 is changed from the unlocked state to the locked state by pressing down the unlocking switch 3. In such aspect, the control element 6 acquires the representative point only by that the imaging operator U decides the relative location of the table 2 and locks the table 2 at the adequate location relative to the desired pathway (i.e., suspends the unlocked state of the table 2), so that the operator can register easily the pathway information.

In addition, according to the aspect of the Embodiment 1, as set forth above, the X-ray imaging apparatus further comprises a unlocking switch 3 that allows looking of the table 2 to be unlocked in the state in which the unlocking element (unlocking switch 3) is being pressed down. According to such aspect, the table 2 moves only while the unlocking switch 3 is being pressed down, so that the table 2 would not relatively move unless the imaging operator U presses down the unlocking switch. Accordingly, an unintentional moving of the table 2 against the imaging operator U can be prevented.

In addition, according to the aspect of the Embodiment 1, as set forth above, the control element 6 registers the pathway information based on a plurality of the representative points (e.g., the starting point D0, the representative points D1, D2, D3 and so forth). According to such aspect, the imaging operator U can easily set up the pathway by, designating the representative points along the imaging target region of the subject S.

In addition, according to the aspect of the Embodiment 1 as set forth above, the direction of relative moving of the table 2 relative to the X-ray irradiation detection element 1 includes the first direction and the second direction (x-direction and y-direction) which are orthogonal to each other in the loading plane. According to such aspect, when X-ray-imaging the subject S, the control element 6 controls the table driving element 5*b* (driving element 5) to move the table 2 based on the pathway information, which is pre-registered relative to both first direction and second direction orthogonal to each other, so that an occurrence of workload in which the imaging operator U operates to relatively move in the two directions including the first direction and the second direction (x-direction and y-direction), is preventable, when imaging.

In addition, according to the aspect of the Embodiment 1 as set forth above, the control element 6 stores the relative location of the table 2, which is acquired in advance separately from the representative points, as the memory location D*, moves the table 2 to the memory location D* by the table driving element 5*b* (driving element 5) at the beginning of acquisition of a plurality of representative points or in the middle thereof, and in addition, acquires the memory location D* as a representative point. According to such aspect, the representative point can be registered based on the memory location D* acquired, in advance, so that a work to register can be eliminated. Particularly, when the memory location D* is a common point existing in an approximate same location relative to each subject S (a characteristic point common to human body), the imaging operator U can register the memory location D* regardless expertise of the operator. Specifically, the pathway including the memory location D* can be easily acquired.

In addition, according to the aspect of the Embodiment 1 as set forth above, when a plurality of representative points is acquired and when the second representative point (e.g., the representative point D40 in FIG. 6) is acquired so that the location of the representative point is returned along the longitudinal direction (x-direction in FIG. 6) from the first direction and the second direction (x-direction and y-direction) orthogonal to each other in the loading plane of the table following acquisition of one or a plurality of representative points (e.g., referring to FIG. 6, the representative points D10, D20, D30), the control element 6 does not use the first representative point (e.g., the representative points D20, D30 in FIG. 6), which is one or a plurality of representative points acquired prior to returning the location and is located in the traveled location farther from the second representative point in the longitudinal direction, to register the pathway information. According to such aspect, when the imaging operator U acquires the deviated location from the desired pathway (erroneous location) as the first representative location, the operator can cancel the erroneously acquired first representative point without separately implementing a canceling operation for the erroneously acquired first representative point. Specifically, a work to re-register the pathway information can be eliminated.

In addition, according to the aspect of the Embodiment 1, as set forth above, the control element 6 controls the velocity of the relative moving between the table 2 and the X-ray irradiation detection element 1 by the driving element 5 based on the operation of the velocity operation element 71. According to such aspect, the imaging operator U can implement the velocity control of the relative moving between the table 2 and the X-ray irradiation detection element 1 by the driving element 5, so that the imaging operator U facilitates to follow the Imaging location on the pathway relative to the velocity of the moving imaging target when implementing an X-ray imaging of the moving imaging target, such as a contrast agent and so forth flowing in blood vessel V of the subject S.

In addition, according to the aspect of the Embodiment 1 as set forth above, the control element 6 acquires the pathway by interpolating with the straight line between representative points. Accordingly, the imaging operator U can set up easily the pathway by interpolating without designating many representative points.

Embodiment 2

Next, the inventor sets forth a constitution of the X-ray imaging apparatus 200 according to the aspect of the Embodiment 2 of the present invention. According to the aspect of the Embodiment 2, the inventor sets forth an example in which a representative point is acquired when the unlocked state is being kept for the predetermined time after the table 2 is made re-locked (the unlocking switch is not being pressed down.

Here, referring to FIGS. 1, 2, relative to the X-ray imaging apparatus 200 according to the Embodiment 2, the control element 61 acquires the representative point when the locked state is maintained for a predetermined time period after the unlocking element changes locking of the table 2 from the unlocked state to the locked state (in which the unlocking switch 3 is being pressed down) by pressing down, the unlocking switch 3 when the representative point is acquired based on that locking of the table 2 is changed from the unlocked state to the locked state by pressing down the unlocking switch 3.

Specifically, the imaging operator U moves the table 2 so that the approximate center of the imaging range is on the expected pathway on imaging by unlocking the locking of the table by pressing down the unlocking switch 3 following initiating the registration processing. Then, the imaging operator U moves the relative location of the table 2 so that the approximate center of the imaging range is on the expected pathway; suspends pressing down the unlocking switch 3 and for example; and registers the information of the location (location in the x-direction and the y-direction), at which the table 2 suspends, as the representative point, when the locked state of the table 2 is maintained for 3 seconds (predetermined time period). At this time, the imaging operator U is informed that the registration is implemented through at least one of sounds from a speaker, not shown in FIG., a message on the message window 73 and a display-color change on the display element 8 and so forth. Further, the waiting time, the predetermined time period, by the time when the representative point is registered is not essential to be 3 seconds and the imaging operator U may set up arbitrarily such period as wished.

In addition, other structure according to the aspect of the Embodiment 2 is the same as the aspect of the Embodiment 1.

(Effect According to the Aspect of the Embodiment 2)

The following effect can be obtained according to the aspect of the Embodiment 2.

In addition, according to the aspect of the Embodiment 2 as set forth above, the control element 61 acquires the representative point when the unlocked state is maintained for a predetermined time period after locking of the table 2 is changed from the unlocked state to the locked state (i.e., in which the unlocking switch 3 is not being pressed down and the table 2 suspends to move) by pressing down the unlocking switch 3 when the representative point is acquired based on that locking of the table 2 is changed from the unlocked state to the locked state by pressing down the unlocking switch 3. According to such aspect, the control element 61 acquires representative point when the unlocked state is maintained for the predetermined period after unlocking of the table 2 lock is changed from the unlocked state to the locked state by pressing down the unlocking switch 3, so that it can be prevented that the representative point is immediately registered even when the imaging operator U erroneously makes the unlocked state by suspending to press down the unlocking switch 3 by unlinking a hand and so forth.

Further, other effects according to the aspect of the Embodiment 2 is the same as the aspect of the Embodiment 1.

Embodiment 3

Figure 10:
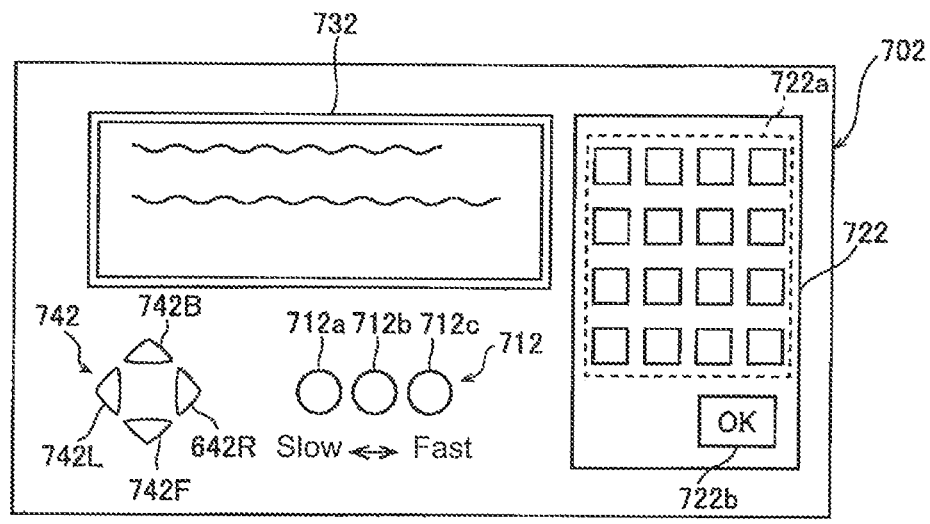
FIG. 10 is a schematic view illustrating an operation element according to the aspect of the Embodiment 3 of the present invention.

Next, referring to FIG. 10, the inventor illustrates the constitution of the X-ray imaging apparatus 300 according to the aspect of the Embodiment 3 of the present invention. According to the aspect of the Embodiment 3, the inventor sets forth an example in which the relative moving of the table 2 is implemented by the table driving element 5b when a representative point is acquired.

Referring to FIG. 10, an operation element 702 comprises a velocity operation switch 712a, a keyboard element including a variety of operation keys 722a and decision keys 722b, and a messaging window 732.

Here, an X-ray imaging apparatus 300 according to the aspect of the Embodiment 3 comprises a direction specification switch 742 that moves relatively an X-ray irradiation detection element 1 and the table 2. The direction specification switch 742 allows the X-ray irradiation detection element 1 and the table to move relatively and in addition, specifies the direction in which the X-ray irradiation detection element 1 and the table 2 move relatively by the driving element 5. And the control element 62 moves at least one of the X-ray irradiation detection element 1 and the table 2 at the predetermined rate in the direction specified by the direction specification switch 742 by the driving element 5 and in addition, acquires the relative location, at which the X-ray irradiation detection element 1 and the table 2 suspend, as the representative point after the direction specification switch 742 is changed from the operative state to the non-operative state, while being in the operative state in which the direction specification switch 742 specifies the direction of relative moving of the X-ray irradiation detection element 1 and the table 2. In addition, the direction specification switch 742 is an example of an "direction specification element" in the claims.

Specifically, while each of direction specification switch 742L, 742R, 742F, 742B corresponding to each moving direction included in the direction specification switch 742 is being pressed down, the table driving element 5b relatively moves the table 2 respectively leftward x1-direction), rightward (x2-direction), backward (y1-direction), and forward (y2-direction). Specifically, each of direction specification switch 742L, 742R, 742F, 742B is operative while being pressed down. In addition, even when the imaging operator U suspends to press down any direction specification switch 742, the table 2 does not suspend immediately and instead gradually brakes and suspends following a slight move.

In addition, the direction specification switches 742L, 742R, 742F, 742B keeps unlocking of the table 2 while any direction specification switches 742L, 742R, 742F, 742B is being pressed down, so that when the direction specification switches 742L, 742R, 742F, 742B are switched contiguously, moving of the table 2 is maintained. Specifically, the location at which the table 2 suspends in the state, in which all direction specification switches 742 are taken off, is registered as the representative point. In addition, for example, when the direction specification switches 742L and 742B are pressed down simultaneously, the table 2 moves right-backward (x1+y1 direction) from the imaging operator U.

In addition, other structure according to the aspect of the Embodiment 3 is the same as the aspect of the Embodiment 1.

(Effect According to the Aspect of the Embodiment 3)

The following effect can be obtained according to the aspect of the Embodiment 3.

In addition, according to the aspect of the Embodiment 3 as set forth above, the relative location at which the X-ray irradiation detection element 1 and the table 2 suspend is acquired as the representative point after the direction specification switch 742 is changed from the operative state to the non-operative state. According to such aspect, the control element 62 acquires the location, at which the table 2 suspends, as the representative point after the direction specification switch 742 is changed from the operative state to the non-operative state, so that even when the table 2 is relatively moved by the driving element 5 but not manually, workability of the work to register the pathway information can be easily improved.

Further, other effects according to the aspect, of the Embodiment 3 is the same as the aspect of the Embodiment 1.

Alternative Embodiment

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the Embodiment 1-3, the location, at which the table 2 suspends, is acquired as the representative point based on that the locking of the table 2 is changed to the unlocked state to the locked state after the table 2 is relatively moved, but the present invention is not limited thereto. According to the present invention, the location (location at beginning of moving), at which the table 2 is suspending, can be acquired as the representative point to relatively move the table 2 to the location corresponding to the next representative point based on the unlocking state of the locking of the table 2 by pressing down the unlocking switch 3 again after locking of the table 2 is changed from the unlocked state to the locked state. In addition, the location (location at beginning of moving), at which the table 2 is suspending, can be acquired as the representative point based on the operation in which locking of the table 2 is unlocked by pressing down the unlocking switch 3 again and locking of the table 2 is locked by not pressing down the unlocking switch 3 (i.e., take off right after the unlocking switch 3 is pressed down) as in the state in which the table 2 is not moved after locking of the table 2 is changed from the unlocked state to the locked state.

In addition, according to the aspect of the Embodiment 3 as set forth above, when the table 2 is moved by the table driving element 5b on acquiring the representative point, the X-ray imaging apparatus 300 (control element 62) acquires the representative point when the table 2 suspends, after the state in which the direction specification switch 742 is being pressed down (operative state) changes to the state in which the direction specification switch 742 is no pressed down (non-operative state), but the present invention is not limited thereto. According to the aspect of the present invention, even when the table 2 is moved by the table driving element 5b on acquisition of the representative point, the representative point can be acquired when the state, in which the direction specification switch 742 is not being pressed down (non-operative state), is maintained for the predetermined period in addition to suspension of moving of the table 2.

Figure 11:
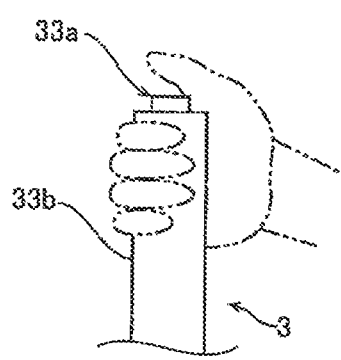
FIG. 11 is a schematic view illustrating the unlocking element according to the aspect of an alternative Embodiment of the Embodiment 1-3 of the present invention.

In addition, according to the aspect of the Embodiment 1-3 as set forth above, referring to FIG. 2, the example is set forth, in which a convex element (salient) is directly and upward installed on the operation base 2b and pressed down from the upper side to the lower side by the imaging operator U (e.g., by palm), but the present invention is not limited thereto. According to the aspect of the present invention, referring to FIG. 11, a grip-type unlocking switch 333, which is gripped by an imaging operator U, including the push-bottom element (unlocking switch) 3a and a grip element 3 can be applied.

In addition, according to the aspect of the Embodiment 3 as set forth above, the direction specification switches 742 comprise the direction specification switch 742L, 742R, 742B and 742F, but the direction specification switch 742 can be a joystick (a lever to move the table 2 in the tilted direction).

In addition, according to the aspect of the Embodiment 1-3 as set forth above, the location turns back relative to the longitudinal direction (x-direction) and is in the traveled location relative to the longitudinal direction, so that two first representative points (representative point D20, D30) are not used to register the pathway information, but the present invention is not limited thereto. According to the present invention, the location turns back relative to the longitudinal direction and is in the traveled location relative to the longitudinal direction, so that the first representative points that are not used to register the pathway information are not limited 2 and can be the number other than 2.

In addition, according to the aspect of the Embodiment 3 as set forth above, the example is set forth, in which when the relative location at which the X-ray irradiation detection element 1 and the table 2 suspend is acquired as the representative point after the direction specification switch 742 is changed from the operative state to non-operative state, the representative point is acquired based on that the direction specification switch 742 is changed to the unlocked state to the locked state, but the present invention is not limited thereto. According to the aspect of the present invention, the representative point can be acquired based on that the direction specification switch 742 is changed from the operative state to the non-operative state and reinstates the operative state.

In addition, according to the aspect of the Embodiment 1-3 as set forth above, the example, in which when the pathway information is acquired, the representative point is acquired by moving the table 2 to the memory location D* stored in the memory element 6b in the middle of acquisition of the representative point by moving the table 2 manually, is set forth, but the present invention is not limited thereto. According to the aspect of the present invention, the starting point D00 of imaging and the representative point D50 acquired at last can be acquired based on the storing location. In addition, when the starting point D00 of imaging and all representative points D10-D50 are acquired based on the storing location, moving of the table prior to the actual imaging (on acquisition of the representative point) can be skipped.

In addition, according to the aspect of the Embodiment 1-3 as set forth above, the example, in which an X-ray imaging of the lower leg of the lying subject S is implemented, but the present invention is not limited thereto.

According to the present invention, an arm (upper leg), an abdomen, other regions of the subject S other than the lower leg of the subject S can be subject to an X-ray imaging, in addition, an image of the standing or sitting subject S can be taken.

In addition, according to the aspect of the Embodiment 1-3 as set forth above, the example of that a relatively weak X-ray is irradiated from the X-ray irradiation element 1a upon the registration operation of the pathway is set forth, but the present invention is not limited thereto. According to the present invention, the X-ray irradiation detection element 1 can further include a lighting device (not shown in FIG.) that irradiates the light to the subject without irradiating an X-ray from the X-ray irradiation element 1a upon the registration operation of the pathway. Accordingly, the imaging area of the subject S can be identified without using an X-ray irradiation.

In addition, according to the aspect of the Embodiment 1-3 as set forth above, the example of that the distance between the representative points is interpolated by the straight line is set forth, but the present invention is not limited thereto. According to the present invention, the curve line other than the straight line can be applied to interpolate the distance between representative points. In such case, for example, the curve line that is smooth at the location of each of representative point (each curvature is the same before and after passing the representative point) can be used, for interpolation.

In addition, according to the aspect of the Embodiment 1-3 as set forth above, the example of that the table 2 is relatively moved in the first direction and the second direction (x-direction and y-direction) in which the table 2 is horizontal to the X-ray irradiation detection element 1 so that the X-ray imaging is implemented from the starting location of imaging and the end location of imaging on the pathway when the representative point is acquired and the actual imaging is implemented, but the present invention is not limited thereto. According to the aspect of the present invention; the table 2 can be relatively moved in the vertical direction to the loading plane (z-direction) when the representative point is acquired and the actual imaging is implemented. In such case, the table 2 can be relatively moved in the third direction in addition to the first direction and the second direction. Specifically, the table 2 can be relatively moved in three-dimensional all directions (X-direction y-direction and z-direction) relative to the X-ray irradiation detection element 1 when the representative point is acquired and the actual imaging is implemented, In addition, according to the aspect of the Embodiment 1-3 as set forth above, the example of that the table 2 is relatively moved relative to the X-ray irradiation detection element 1 by the table driving element 5b so that the X-ray imaging is implemented from the starting location of imaging and the end location of imaging on the pathway when the representative point is acquired and the actual imaging is implemented, but the present invention is not limited thereto. According to the aspect of the present invention, if needed, the location and the angle of the X-ray irradiation detection element 1 (arm element 1c) is moved by the irradiation detection driving element 5a so that the table 2 can be relatively moved relative to the X-ray irradiation detection element 1. At this time, each of the table 2 and the X-ray irradiation detection element 1 (arm element 1c) can be simultaneously moved by the irradiation detection driving element 5a and the table driving element 5b. Specifically, the subject S loaded on the table 2 and the irradiation location of the X-ray by the X-ray irradiation detection element 1 can be relatively moved by shifting each location of the table 2 and the X-ray irradiation detection element 1. In addition, for example, the table 2 is moved and when the representative point is acquired and the X-ray irradiation detection element 1 can be moved when the actual imaging is implemented, In addition, according to the aspect of the Embodiment 1-3 as set forth above, the example of that the X-ray irradiation element 1a irradiates X-ray approximately vertically to the loading plane of the subject S when the representative point is acquired and the actual imaging is implemented is set forth, but the present invention is not limited thereto. According to the aspect of the present invention, regardless of the locational relationship in FIG. 1, the X-ray irradiation element to can irradiate an X-ray not-vertically to the loading plane of the subject S. In such case, the table 2 can be relatively moved, in the first direction and the second direction orthogonal to each other in the vertical plane, which is not the loading plane, relative to the X-ray irradiation direction. In addition, the X-ray detection element 1b can be moved to under side of the X-ray irradiation element 1a to implement imaging.

In addition, according to the aspect of the Embodiment 1-3 as set forth above, the X-ray imaging apparatus comprising a single plane aspect, in which an X-ray imaging is implemented by the X-ray irradiation detection element 1 including a pair of X-ray irradiation element 1a and X-ray detection element 1b, is set forth, but the present invention is not limited thereto. According to the aspect of the present invention, the X-ray imaging apparatus comprising a bi-plane aspect, in which the X-ray irradiation, detection element 1 including two pairs of X-ray irradiation element 1a and X-ray detection element 1b providing different X-ray irradiation direction to each other implements an X-ray imaging, can be provided. In addition, the X-ray irradiation detection element 1 including at least three pairs of X-ray irradiation element 1a and X-ray detection element 1b providing different X-ray irradiation direction to each other implements an X-ray imaging can implement an X-ray imaging.

In addition, according to the aspect of the Embodiments 3 set forth above, an example of that the table 2 is moved by the direction specification switch 742 is set forth, but the present invention is not limited thereto. According to the aspect of the present invention, the direction specification switch 742 can move the X-ray detection element 1.

In addition, according to the aspect of the Embodiments 1 to 3 as set forth above, for convenience of explanation, the inventors set forth a processing of the X-ray imaging apparatus according to the present invention is processed in order following the process flow using the flow driving-type flow chart, but the present invention is not limited thereto. According to the present invention, the processing operation can be performed using an event driving-type processing (event driven type) every event. In such case, a perfect event driven type can be applied or a combination of event driving and flow driving can be applied.

REFERENCE OF SIGNS

1 X-ray irradiation detection element
1a X-ray irradiation element
1b X-ray detection element
2 Table
3, 33 Unlocking switch (Unlocking element)
5 Driving element
6, 61, 62 Control element 71, 712 Velocity operation element
100, 200, 300 X-ray imaging apparatus
742 Direction specification element
D1, D10, D11, D2, D20, D21, D3, D30, D31, D40, D50, D60 Representative point
D20, D30 Representative point (first representative point)
D40 Representative point (second representative, point)
D* Memory location
S Subject *

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The computer readable media can be an article comprising, a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
   an X-ray irradiation detection element including an X-ray irradiation element that irradiates an X-ray to a subject and an X-ray detection element that detects said X-ray transmitting through said subject;
   a table that is enabled to load said subject on a loading plane;
   a driving element that relatively moves said table relative to said X-ray irradiation detection element; and
   a control element that controls a to move of at least one of said table and said X-ray irradiation detection element by said driving element based on a pre-registered pathway information when imaging said subject;
   wherein said control element acquires an information as a representative point that is relative to a location at which said table and said X-ray irradiation detection element suspend moving relative to each other y based on either that a relative moving between said table and said X-ray irradiation element suspends, or that once the relative moving between said table and said X-ray irradiation detection element is suspended and then said relative moving between said table and said X-ray irradiation detection element restarts after said table and said X-ray irradiation detection element are relatively moved by at least one of a manual element and or a driving element, and registers said pathway information based on said acquired representative point.

2. The X-ray imaging apparatus, according to claim 1, further comprising;
   an unlocking element that unlocks locking of said table to make movable so that said X-ray irradiation detection element and said table are relatively movable; and
   wherein said control element acquires an information of location, at which said table suspends, as a representative point; and registers a pathway information based on said acquired representative point, based on at least one of that a locking of said table is unlocked by said unlocking element to move said table, and that a locking of said table is changed again to the unlocked state after locking of said table changes from the unlocked state to the locked state by said unlocking element.

3. The X-ray imaging apparatus, according to claim 2, wherein:
   said control element acquires said representative point simultaneously when said unlocking element changes locking of said table from the unlocked state to the locked state when said representative point is acquired based on that said locking of said table changes from the unlocked state to the locked state by said unlocking element.

4. The X-ray imaging apparatus, according to claim 2, wherein:
   said control element acquires said representative point when the locked state is maintained for a predetermined time period simultaneously after said unlocking element changes said locking of said table from the unlocked state to the locked state when said representative point is acquired based on that locking of said table is changed from the unlocked state to the locked state by said unlocking element.

5. The X-ray imaging apparatus, according, to claim 2, wherein:
   said unlocking element, further comprises:
      a unlocking switch that makes locking of said table unlocked while said unlocking switch is being pressed down.

6. The X-ray imaging apparatus, according to claim 1, wherein:
   said control element registers said pathway information based on a plurality of said representative points.

7. The X-ray imaging apparatus, according to claim 1, wherein:
   a direction of relative moving of said table relative to said X-ray irradiation detection element comprising at least one of a first direction and a second direction in a loading plane of said table in which said table moves; and
   said first and said second directing being orthogonal to each other in said loading plane of said table among a plurality of directions, in which said table moves, and orthogonal to each other.

8. The X-ray imaging apparatus, according to claim 1, further comprising:
   a plurality of direction specification elements that move relatively said X-ray irradiation detection element and said table; and
   wherein said direction specification element makes said X-ray irradiation detection element and said table movable relatively to each other and which specifies a direction in which said X-ray irradiation detection element and said table are relatively moved by said driving element;
   said control element controls said driving element to move at least one of said X-ray irradiation detection element and said table at a predetermined rate in the direction specified by said direction specification element by said driving element; and acquires a relative location, at which said X-ray irradiation detection element and said table suspend moving, as said representative point after said direction specification element is changed from an operative state to a non-operative state, while a direction of relative moving of said X-ray irradiation detection element and said table is being specified and made operative by said direction specification element.

9. The X-ray imaging apparatus, according, to claim 1, wherein:
   said control element stores a relative location between said table and said X-ray irradiation detection element, which is acquired in advance separately from said representative point, as a memory location, moves relatively said table and said X-ray irradiation detection element by said driving element at beginning or in the middle of acquisition of a plurality of said representative points, and acquires said memory location as said representative point.

10. The X-ray imaging apparatus, according to claim 1, wherein:
    said control element does not use a first representative point that is at least one of a plurality of first representative points acquired before a location is returned and is located in a traveled location farther from a second representative point to register said pathway information when said second representative point is acquired so that the location of said representative point is returned along a longitudinal direction among a plurality of directions orthogonal to each other in which said table moves following acquisition of at least one of a plurality of said fast representative points when a plurality of said representative points are acquired.

11. The X-ray imaging apparatus, according to claim 1, further comprising:
    a velocity operation element that receives an operation to control a velocity of relative moving between said table and said X-ray irradiation detection element moving along a pathway based on said pathway information; and
    wherein said control element controls a velocity of relative moving between said table and said X-ray irradiation detection element by said driving element based on an operation of said velocity operation element.

12. The X-ray imaging, apparatus, according to claim 1 wherein:
    said control element acquires said pathway based on said pathway information by interpolating a distance between said representative points with at least one of a straight line and a curved line.

13. An imaging method, using an X-ray imaging apparatus having an X-ray irradiation detection element including an X-ray irradiation element that irradiates an X-ray to a subject and an X-ray detection element that detects said X-ray transmitting said subject, of which said X-ray irradiation detection element and said table are relatively movable, comprising the steps of:
    acquiring the information as a representative point relative to a location at which said table and said X-ray irradiation detection element suspend to move relatively based on that relative moving between said table and said X-ray irradiation element suspends; or that once the relative moving between the table and the X-ray irradiation detection element suspends, said relative moving between said table and said X-ray irradiation detection element restarts after said table and said X-ray irradiation detection element are relatively moved; and
    registering a pathway information in advance based on said acquired representative point; and
    a step of implementing an X-ray imaging said subject while moving at least one of said table and said X-ray irradiation detection element by said driving element based on a pre-registered pathway information.

* * * * *